US006593274B2

(12) United States Patent
Policello

(10) Patent No.: US 6,593,274 B2
(45) Date of Patent: *Jul. 15, 2003

(54) TERMINALLY MODIFIED, AMINO, POLYETHER SILOXANES

(75) Inventor: George A. Policello, Ossining, NY (US)

(73) Assignee: Crompton Corporation, Middlebury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/812,436

(22) Filed: Mar. 20, 2001

(65) Prior Publication Data

US 2001/0029238 A1 Oct. 11, 2001

Related U.S. Application Data

(60) Continuation of application No. 09/513,275, filed on Feb. 24, 2000, now Pat. No. 6,235,681, which is a division of application No. 09/209,061, filed on Dec. 10, 1998, now Pat. No. 6,238,684.

(51) Int. Cl.$^7$ .................. A01N 63/00; A01N 25/24; A01N 25/00; B01D 19/04; B01D 12/00

(52) U.S. Cl. .............. 504/116; 424/405; 424/407; 516/198; 516/124; 516/204; 516/203

(58) Field of Search .............. 504/116; 424/405, 424/407; 516/198, 124, 204, 203

(56) References Cited

U.S. PATENT DOCUMENTS 5,998,331 A * 12/1999 Policello .................. 504/116
6,235,681 B1 * 5/2001 Policello .................. 504/116

* cited by examiner

*Primary Examiner*—Russell Travers
*Assistant Examiner*—Shengjun Wang
(74) *Attorney, Agent, or Firm*—Michael P. Dilworth

(57) ABSTRACT

The present invention teaches the composition of terminally modified, amino, polyether, siloxanes, known hereforth as amino siloxane alkokylates, and their use as adjuvants. The amino siloxane alkoxylates of the present invention enhance the efficacy of agrichemicals on plants as compared to conventional TSE's alone. The amino siloxane alkoxylates have at one end, an amine functionality and at the other end, a polyalkyleneoxide functionality.

22 Claims, No Drawings

TERMINALLY MODIFIED, AMINO, POLYETHER SILOXANES

This is a continuation of application U.S. Ser. No. 09/513,275 filed Feb. 24, 2000 now U.S. Pat. No. 6,235,681 which is a division of U.S. Ser. No. 09/209,061 filed Dec. 10, 1998 now U.S. Pat. No. 6,238,684, incorporated herein by reference.

BACKGROUND OF THE INVENTION

Many herbicides require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, or to provide penetration of the herbicide into the plant cuticle. These adjuvants are provided either as a tankside additive or used as a component in herbicide formulations.

Gaskin, et al., (*Pestic. Sci.* 1993, 38; 185–192) demonstrated that some trisiloxane ethoxylates (TSE), such as Silwet L-77® surfactant (available from OSi Specialties, Inc. of Greenwich, Conn.), can antagonize cuticular penetration of a herbicide into grasses, when compared to the herbicide alone. The term antagonism is used to indicate that the treatment of herbicide plus adjuvant is less effective than the comparative herbicide treatment.

Gaskin, et al., (*Pest. Sci.* 1993, 38, 192–200) showed that this antagonism can be mitigated if the number of ethylene oxide (EO) units contained in the TSE is increased to 17 or more; however, superspreading of the TSE is reduced dramatically once the degree of ethoxylation exceeds about 12 EO, and TSE's containing the higher EO adducts show spreading properties similar to conventional nonsilicone surfactants.

Sandbrink, et al., (*Pest. Sci.* 1993, 38, 272–273) published that a TSE antagonized glyphosate performance relative to glyphosate alone in the control of *Panicum maximum* Jacq. Snow, et. al., *Langmuir*, 1993, 9, 424–30, discusses the physical properties and synthesis of novel cationic siloxane surfactants. These siloxanes are based on the reaction of a chloropropyl modified trisiloxane with an alkanolamine, such as N-methylethanolamine, which was further reacted with a halide to make a quaternary surfactant.

Petroff, et al., (EP 92116658) describes the use of cationic, quaternary trisiloxanes to enhance the efficacy of glyphosate on velvetleaf, a broadleaf weed. Henning, et al., (DE4318537) describes cationic siloxanyl modified polyhydroxy hydrocarbon or carbohydrate for use with plant protection agents. These compounds are derived from a saccharide containing 1 to 10 pentose and/or hexose units, modified with a quaternary ammonium group, and a siloxane moiety.

Reid. et al., (U.S. Pat. No. 3,389,160) describes amino modified siloxane alkoxylates where the amino functionality appears as the terminal group on the alkyleneoxide moiety, opposite the siloxane group.

Policello in PCT WO 97/32475 discloses amino modified siloxanes wherein the amine is bound by an ether bond to the siloxane backbone wherein the amine may be terminal or pendant to the backbone.

SUMMARY OF THE INVENTION

The present invention teaches the composition of terminally modified, amino, polyether, siloxanes, known henceforth as amino siloxane alkokylates, and their use as adjuvants. The amino siloxane alkoxylates of the present invention enhance the efficacy of agrichemicals on plants as compared to conventional TSE's alone. Optionally, the amino siloxane alkoxylates of this invention may be blended with conventional trisiloxane alkoxylates. Blends of these unique amino siloxanes with more traditional trisiloxane alkoxylates (TSA) provide superspreading properties, on difficult to wet surfaces, that are equal to, or greater than what is contributed by the individual components.

DETAILED DESCRIPTION OF THE INVENTION

These compositions are especially useful in overcoming the antagonistic effects on pesticide efficacy associated with superspreading, TSAs. Mixtures of the compositions of the present invention with TSAs provide enhanced spreading properties relative to the individual components alone. In addition, these products provide a low aqueous surface tension ($\leq 25$ mN/m at 0.1 wt %), which is desirable for enhanced spreading of pesticide solutions.

COMPOSITION

The amino siloxane alkoxylates of the present invention have the average general formula: $ZMe_2SiO[(Me)_2SiO]_x SiMe_2Q$, wherein $x=0$ to 2, preferably 1. $Q=C_aH_{2a}O(C_2H_4O)_b(C_3H_6O)_cR$, $a=2$ to 4, preferably 3, $b=1$ to 12, preferably 3 to 8, $c=0$ to 5, providing that when c is $>0$, $(b+c)=2$ to 12, preferable $=4$ and 8, R is hydrogen, acetyl or a hydrocarbon radical between 1 and 4 carbon atoms, Z is $BN[DO(C_dH_{2d}O)_eR]_{2-z}V_z$, each d is 2 to 4, preferably 2 to 3, each e is 0 to 15, preferably 0 to 8, $z=0$ to 2, preferably 2, each V is a univalent group, D is an alkylene divalent bridging group on which there may be hydroxyl substituents, and B is a divalent bridging group.

V groups preferably are alkyl (which may be branched, linear or cyclic) of less than 8 carbons, which may or may not contain hydroxyl functionalities. Another preferred V is an alkyl amine functionality, the nitrogen of which may be further substituted (e.g. with an alkyl) or be further alkoxylated. Exemplary V are ethyl, 2-hydroxyethyl, 3-hydroxypropyl, methyl, and 2-aminoethyl.

B groups may be of the formula $D(O)_y(C_dH_{2d}O)_jD$ wherein D and d are as above, $j=0$ to 8, preferably 0 to 2, and $y=0$ or 1. Preferably D has 2 to 6 carbon atoms, B may also preferably be a divalent alkylene group of $C_2$–$C_4$.

When Q or B is a mixture of oxyalkylenes, it may be blocked or random. One skilled in the art will understand the advantages in the position of the oxyethylene relative to the oxypropylene, when the alkyleneoxide croup is blocked.

The Z groups may include protonated amines, i.e, where there is a hydrogen ion attached to the nitrogen in the Z group, which can occur to the amino siloxane alkoxylates under acidic conditions. Also contemplated herein are quaternary versions of Z, i.e., where there is a third $R^3$ group on the nitrogen in Z, but said quaternary compounds are not preferred for use in the present invention.

Preferred Z structures are wherein R is hydrogen or methyl, D is a divalent organic group of 2 to 4 carbons, B is a divalent organic group of 2 to 4 carbons, in which at least one carbon radical contains a hydroxyl group, and V is 2-hydroxyethyl, 2-hydroxypropyl, 3-hydroxypropyl, propyl, ethyl or methyl. Preferred amino siloxane alkoxylates are trisiloxanes.

In addition the compositions of the present invention optionally may include nonionic siloxane alkoxylates of the general formula:

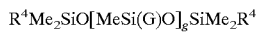

$R^4Me_2SiO[MeSi(G)O]_gSiMe_2R^4$ wherein g=0 to 2, preferably 1, $G=C_2H_{2a}O(C_2H_4O)_t(C_3H_6O)_wR$, a and R are as above, t=3 to 12, preferably 4 to 8, w=0 to 8, providing that when w is >0, (t+w) is preferably between 5 and 12. $R^4$ is G, or an alkyl of one to four carbons. The preferred nonionic siloxane alkoxylates are trisiloxane alkoxylates, where g=1, d=3, t=4 to 8, w=0, $R^4$ is Me, R is H or Me.

The compositions of the present invention also optionally include ingredients for use herein are pesticides, especially acid functionalized ones, i.e., compounds that contain at least one carboxylic, sulfonic or phosphonic acid group or their salt or ester. The term pesticide means any compound used to destroy pests, e.g., rodenticides, fungicides, and herbicides. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

MANUFACTURE

The amino siloxane alkoxylates of the present invention may be made by the hydrosilation of a terminal hydridosiloxane with allyl glycidal ether, and allyl started polyalkyleneoxide. This is followed by ring opening of the epoxide moiety with a primary or secondary amine. The components described are available commercially and may be made as known in the art. Alternatively, the hydrosilation may take place with an allyl amine and an allyl started polyalkyleneoxide. Hydrosilation reaction conditions may be found in Marcienic, ed., 122–23 and 558–568 (1995), which is incorporated herein.

The amine intermediate (e.g., allyl amine) may be prepared by reaction of an unsaturated halide (e.g., allyl bromide) and an amine. The allyl amine also may be prepared by reaction of an allyl glycidyl ether (or similar unsaturated epoxide) with an amine (which result in an ether bond in the bridging group B). An alternative method uses aziridine, which is not preferred for toxicity reasons, are disclosed in PCT US97/04128, which is incorporated herein by reference.

The hydrosilation products may be blends of the product of the present invention with amine terminated siloxanes and polyether terminated siloxanes. If desired, one may separate these, e.g., by distillation; however, these blends may be used without such purification.

The nonionic siloxane and the pesticides are available commercially and their manufacture is known in the art.

USE

The amino siloxane alkoxylates primarily are intended for use in the agricultural field as adjuvants for pesticide containing aqueous formulations. The composition of the present invention is useful as a tank side additive, or as a component in a herbicide formulation. In addition the compositions of the present invention are useful as adjuvants for other pesticides, such as, fungicides, insecticides, plant growth regulators, acaracides and the like.

The siloxanes are added directly to a spray tank along with an acid functional pesticide, or as part of a pesticide formulation. When used as a tankside additive, the amino siloxane alkoxylates are present at weight concentrations between 0.01% and 5.0%, preferably between 0.025% and 0.5%. Likewise, when the aminosiloxane alkoxylates are used in a pesticide formulation (In-can), they are present at weight concentrations that will deliver between 0.01% and 5.0% to the final use dilution, preferably between 0.025% and 0.5%, of the final use dilution.

It is noted that most dilutions will be made with water, but in the case of crop oil concentrates, oils will be the diluents.

When the compositions of the present invention are used in conjunction with a nonionic siloxane alkoxylate, the weight ratio of the nonionic siloxane alkoxylate to the amino siloxane alkoxylates is between 5:95 and 95:5, preferably between 5:95 and 40:60. The blend may be accomplished by physically mixing the two components together as a formulation, or by adding them separately to a spray mixture at point of use.

The amino siloxane alkoxylates also may be used generally as surface active agents in aqueous formulation where there is an acid functionalized component. The amino siloxane alkoxylates of the present invention also may be used generally as surface active agents, including, but not limited to, surfactants, wetting agents and softeners for textiles, as flowing and leveling agents in coatings, in hair care products, skin care and creams for personal care applications and as anti-static agents, detergents and softeners for laundry products. Other uses will be obvious to those of skill in the art.

Optionally, the amino siloxane alkoxylates may be blended with other nonionic, cationic or anionic co-surfactants, especially those with hydrophobes of $C_5-C_{10}$ (short chain alkoxylates) and GEMINI surfactants (see WO 97/23281).

EXAMPLES

The following examples are presented to further illustrate and explain the present invention and should not be taken as limiting in any regard. Unless otherwise indicated, all parts and percentages are by weight, and are based on the weight at the particular stage of the processing being described.

Example 1 a. Epoxy Siloxane Alkoxylates Intermediate:

25.0 g (0.1199 moles) of 1,1,3,3,5,5-hexamethyltrisiloxane (>97% by GC) was added to a 250 mL, 4 neck round bottom flask, equipped with a mechanical agitator, a Claisen adapter containing a reflux condenser and a thermometer (with Therm-o-Watch), a nitrogen bypass, and a 100 mL addition funnel containing 13.7 g (0.1199 moles) of allyl glycidal ether (AGE). The 1,1,3,3,5,5-hexamethyltrisiloxane was heated to 65° C. and catalyzed with 0.02 g of platinum catalyst. The AGE then was added dropwise to the reaction mixture which exothermic to a maximum of 72° C. The temperature was maintained by the addition rate of the AGE, and supplemented as needed by a heating mantle. After all of the AGE was added, the temperature was adjusted to 80° C. At this point 10 g (0.0442 moles) of allylpolyethyleneoxide (Allyl=18.2 wt %, Moles EO=4) was added to the flask, along with an additional 0.03 g of platinum catalyst. The reaction exothermed to 82.9° C. within 5 minutes. At this point the temperature was adjusted to 90° C. and the remaining 25.24 g (0.1117 moles) of allylpolyethyleneoxide was added dropwise from the addition funnel to the flask contents. The temperature was maintained between 98° C. and 101° C. by the addition rate of the allylpolyethyleneoxide, and supplemented, as needed, by a heating mantle. Once all of the allylpolyethyleneoxide was added, the temperature was adjusted to 95° C. and stirred for 1 hour. The reaction mixture showed no traces of SiH when introduced to a fermentation tube containing KOH/water/ethanol solution. The product was cooled to 60° C. and treated with 4 g $NaHCO_3$, and stirred for 1 hour. The mixture was filtered through a fine filter pad and stripped on a Rotovap for 1.5 hours at 70° C. and 1.0 mm Hg to afford a clear amber liquid with an epoxy content of 6.0 wt % (92.4% of theory based on initial charge).

b. Amino Siloxane Alkoxylate

The epoxy siloxane intermediate (55.0 g; 0.0825 moles), along with 11.28 g (0.1073 moles) of diethanolamine (corresponding to an 30% molar excess), and 28.4 g of 2-propanol (solvent), were added to a 250 mL, 4 neck round bottom flask, equipped with a mechanical agitator, a Claisen adapter containing a reflux condenser and a thermometer (with Therm-O-Watch), and a nitrogen bypass. The mixture was heated to 80° C., and catalyzed with 0.1 g titanium(IV) butoxide. The reaction time was approximately 6 hours, at which point the temperature was adjusted to 50° C., and 0.5 g water was added to deactivate the catalyst. Mixing time was approximately 1 hour. The product was then filtered through a fine filter pad and stripped on a Rotovap for 1.5 hours at 70° C. and 1.0 mm Hg to afford a clear amber liquid with a Brookfield viscosity of 257 cps at 21° C. (spindle SG-2, 60 rpm).

The structure for the amino siloxane alkoxylate was confirmed by $^{29}Si$ and $^{13}C$ NMR. The amino siloxane alkoxylate used here as an example, is shown as ASA-1, in Table 1. Other compositions of amino siloxane alkoxylates shown below were prepared according to this procedure.

Example 2 a. Composition Examples of Invention

Table 1 describe the amino siloxane alkoxylates used herein as illustrative examples of the compositions of the present invention.

b. Comparative Silicone Based Surfactants:

Table 2 provides structural information on two comparative trisiloxane alkoxylates that are commercially used as wetting agents for agrichemicals. These materials were prepared by standard hydrosilation of an allyl terminated polyether with an Si—H intermediate, such as heptamethyltrisiloxane. The SiH intermediates were prepared by acid equilibration as is known in the art.

TABLE 2

Description of Conventional Trisiloxane Alkoxylates
$Me_3SiO[MeSi(G)O]_1SiMe_3$

| Reference | G Group |
|---|---|
| Sil-A | $C_3H_6O(C_2H_4O)_8CH_3$ |
| Sil-B | $C_3H_6O(C_2H_4O)_8H$ | c. Comparative Nonsilicone Surfactants:

Table 3 provides descriptions of typical, comparative, nonsilicone surfactants, used as agricultural wetting agents.

TABLE 3

Description of Comparative Conventional Nonsilicone Surfactants

| Reference | Moles EO | Remarks |
|---|---|---|
| OPE | 10 | Octylphenol ethoxylate (Triton X-100) (Union Carbide Corp., Danbury, CT) |
| TAE | 15 | Tallow amine ethoxylate (Ethomeen T/25) (Akzo Nobel Chemicals Inc.: Chicago, IL) |

Example 3

Surface Tension

This example compares commonly used surfactants with the amino siloxane alkoxylate (ASA) compositions of the present invention for their ability to provide a reduction of the aqueous surface tension to values $\leq 25$ mN/m, which is necessary for enhanced spreading of pesticide solutions (Table 4). The aqueous surface tension was determined by the Wilhelmy plate method, using a sand blasted platinum blade as the sensor. Surfactant solutions (0.1 wt %) were prepared in 0.005 M sodium chloride solution either alone or as mixtures. The mixtures of the ASA component and SIL-B were prepared by blending 0.1 wt % solutions of the individual surfactants at a ratio of 80/20 (ASA/SIL-B).

TABLE 1

Description of Amino Siloxane Alkoxylates

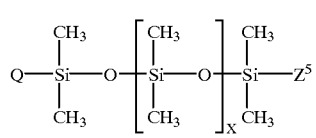

| Reference | X | Q Group | Z Group |
|---|---|---|---|
| ASA-1 | 1 | $C_3H_6O(C_2H_4O)_4H$ | $C_3H_6OCH_2CH(OH)CH_2NV_2$ |
| ASA-2 | 1 | $C_3H_6O(C_2H_4O)_5H$ | $C_3H_6OCH_2CH(OH)CH_2NV_2$ |
| ASA-3 | 1 | $C_3H_6O(C_2H_4O)_5(C_3H_6O)_{2.5}H$ | $C_3H_6OCH_2CH(OH)CH_2NV_2$ |
| ASA-4 | 0 | $C_3H_6O(C_2H_4O)_4H$ | $C_3H_6OCH_2CH(OH)CH_2NV_2$ |

$V = -C_2H_4OH$

Therefore, Blend-1=ASA-1/SIL-B, Blend 2=ASA-2/SIL-B, Blend-3=ASA-3/SIL-B, and Blend-4=ASA-4/SIL-B (all at a ratio of 80/20).

TABLE 4

Comparison of Surface Tension Properties

| Surfactant | Composition of Invention | Surface[a] Tension |
|---|---|---|
| ASA-1 | Yes | 23 |
| ASA-2 | Yes | 24 |
| ASA-3 | Yes | 23 |
| ASA-4 | Yes | 25 |
| Blend-1 | Yes | 21 |
| Blend-2 | Yes | 20 |
| Blend-3 | Yes | 21 |
| Blend-4 | Yes | 20 |
| Sil-A | No | 21 |
| Sil-B | No | 21 |
| OPE | No | 29 |
| TAE | No | 41 |
| None[b] | N/A | 72 |

[a] Surface tension in mN/m at 25° C.
[b] Surface tension of water from CRC Handbook of Chemistry and Physics; 63 Edition, 1982–1983.

Example 4

In addition the compositions of the present invention provide enhanced spreading when combined with nonionic trisiloxane ethoxylates, meaning that the combination of the two components gives a greater degree of spreading then either of the components alone, at concentrations equivalent to that contained in the mixture (Table 5).

Spreading was determined by applying a 10 μL droplet of surfactant solution to a polyester film (3M, IR 1140 transparency film) and measuring the spread diameter after 30 seconds. The solution was applied with an automatic pipette to provide droplets of reproducible volume. Deionized water that was further purified with a Millipore filtration system was used to prepare the surfactant solutions.

To demonstrate the enhanced spreading observed with blends of the ASA components of this present invention and traditional nonionic trisiloxane ethoxylates, 0.1 wt % solutions of each component were prepared in distilled water. The solutions were blended in various ratios of the AMA component to SIL-B (See Table 5) to achieve the desired blend composition. For example, a blend consisting of 9.0 g ASA-1 (0.1 wt %) was combined with 1.0 g SIL-B (0.1 wt %) to afford a mixture that contained 0.09 wt % ASA-1, plus 0.01 wt % SIL-B (a 90/10 blend ratio). Likewise the comparative is SIL-B alone at concentrations equivalent to what is contained in the corresponding blend. For example, the comparative blend with SIL-B for the 90/10 ratio, combines 9.0 g distilled water with 1.0 g SIL-B. This yields 0.01 wt % SIL-B, which is equivalent to the amount contained in the 90/10 blend.

TABLE 5

Spreading Properties of Amino Siloxane Alkoxylate/SIL-B Blends (0.1 wt % Blend)

| Blend Ratio ASA/SIL-B | ASA-1 + SIL-B | ASA-2 + SIL-B | ASA-3 + SIL-B | ASA-4 + SIL-B | Comparative None + SIL-B* |
|---|---|---|---|---|---|
| 100/0 | 11 | 9 | 8 | nd | NA |
| 90/10 | 13 | 11 | 10 | 10 | 8 |
| 80/20 | 25 | 14 | 14 | 16 | 17 |
| 70/30 | 36 | 23 | 27 | 26 | 17 |
| 60/40 | 30 | 33 | 30 | 32 | 28 |
| 50/50 | 45 | 41 | 30 | 36 | 34 |
| 40/60 | 44 | 44 | 44 | nd | 36 |
| 0/100 | NA | NA | NA | NA | 51 |

*None + SIL-B indicates that water was substituted for the ASA component to provide spreading contributed by SIL-B.

Example 5

Nonionic trisiloxane alkoxylates have been shown to antagonize the uptake of glyphosate into grasses, giving a lower degree of uptake (Gaskin. et al., *Pestic. Sci.* 1993, 38, 185–192), or a lower degree of control then achieved with glyphosate treatments alone. The compositions of the present invention provide enhanced glyphosate activity on grasses relative to trisiloxane ethoxylates or glyphosate alone.

The effect of adjuvant on glyphosate isopropylamine salt (Gly-IPA) efficacy was determined using a barnyardgrass assay. Barnyardgrass (*Echinochloa crus-galli*) was grown in the lab under fluorescent growth lights, and trimmed 11 days after planting, from 9 cm to 4 cm. When the plants reached to 8–9 cm in height (3 days after trimming) they were treated with spray solutions containing either glyphosate alone, or with glyphosate (Gly-IPA at 1.0%, 0.5% and 0.25%), plus a surfactant at 0.1 wt %, using a spray volume of 96 l/ha. Efficacy was determined by visual observation of plant regrowth 2 weeks after treatment, using a rating system were 0 indicates no weed control, and 100% indicates complete control.

Table 6 provides the compositions for the various spray mixtures used to treat barnyardgrass in this example.

TABLE 6

Surfactant Composition for Spray Treatments

| | Wt % | |
|---|---|---|
| Treatment | AMA-1 | SIL-B |
| Treatment-1 | 0.1 | 0 |
| Treatment-2 | 0.08 | 0.02 |
| Treatment-3 | 0.07 | 0.03 |
| Treatment-4 | 0.06 | 0.04 |
| Treatment-5 | 0.05 | 0.05 |
| Treatment-A | 0 | 0 |
| Treatment-B | 0 | 0.1 |

Table 7 demonstrates that the compositions of the present invention (Treatments 1–5) provide an overall significant enhancement to glyphosate response relative to glyphosate alone (Treatment-A), or to the comparative trisiloxane ethoxylate SIL-B (Treatment-B).

TABLE 7

The Effect of Adjuvant on Glyphosate Efficacy on Barnyardgrass 14 Days After Treatment
Percent Barnyardgrass Control

| Treatment | Glyphosate Rate | | | |
|---|---|---|---|---|
| | 1.0% | 0.5% | 0.25% | Mean |
| Treatment-1 | 77.5 a | 42.5 b | 36.3 a | 52.1 a |
| Treatment-2 | 38.8 b | 75.0 a | 36.3 a | 50.0 a |
| Treatment-3 | 80.0 a | 42.5 b | 23.3 a | 48.6 a |
| Treatment-4 | 73.3 a | 42.5 b | 7.5 b | 41.1 a |
| Treatment-5 | 36.3 a | 33.3 c | 5.3 b | 24.9 b |
| Treatment-A | 8.7 c | 28.0 c | 1.0 b | 12.3 c |
| Treatment-B | 8.8 c | 5.0 d | 3.0 b | 5.6 c |

Data with different letters indicate a statistically different result. Data with common letters are not statistically different according to Tukey test (p=0.05).

Example 6

Barnyardgrass (BYG) was treated with glyphosate-isopropylamine salt (0.25%, 0.5% and 1.0%) using 0.1 wt % ASA-1, alone or as mixtures with SIL-B. The applications were made using a spray volume of 103 l/ha. Simulated rainfall (0.25 in.) was applied 2 h after treatment to remove any glyphosate that was not absorbed by the BYG. This was done to determine how effective the treatments were at making glyphosate rainfast (resistant to wash-off), which is associated with the rapid uptake of chemical into the plants. Efficacy was determined by visual observation of plant regrowth 2 weeks after treatment, using a rating system were 0 indicates no weed control, and 100% indicates complete control.

Table 8 indicates that the ASA-1 and its blends with SIL-B are more effective at enhancing glyphosate efficacy on BYG than SIL-B. As anticipated, SIL-B demonstrated the classical antagonism of glyphosate efficacy on grass species, when used with glyphosate rates below 1 wt %. However, even the treatment at 1 wt % glyphosate plus SIL-B, the enhancement in efficacy was not statistically different form glyphosate alone.

TABLE 8

Effect of Adjuvant on Glyphosate-IPA Efficacy on Barnyardgrass (2 Wks after treatment)

| % ASA-1 | % Glyphosate | | |
|---|---|---|---|
| | 1.0 | 0.5 | 0.25 |
| 100 | 99.5 a | 87.5 a | 68.75 a |
| 80 | 83.25 b | 76.75 a | 31.25 bc |
| 70 | 92.25 b | 60.0 a | 32.5 bc |
| 60 | 92.0 b | 77.5 a | 17.5 c |
| 50 | 92.5 ab | 81.0 a | 51.25 ab |
| 0 | 57.5 c | 7.5 b | 8.75 c |
| (100% SIL-β) No Surfactant | 27.5 c | 16.25 b | 15.3 c |

Note:
Mean followed by same letter, within the same column, is not significantly different by Tukey test (p = 0.05).

I claim:

1. A process for treating plants comprising applying to plants a composition comprising an amino siloxane alkoxylate of the following formula:

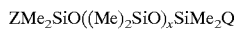

ZMe$_2$SiO((Me)$_2$SiO)$_x$SiMe$_2$Q wherein
x=0 to 2,
Q=C$_a$H$_{2a}$O(C$_2$H$_4$O)$_b$(C$_3$H$_6$O)$_c$R,
a=2 to 4,
b=1 to 12,
c =0 to 5, provided that when c>0, (b+c)=2 to 12,
R is hydrogen, acetyl, or a hydrocarbon radical containing between 1 and 4 carbon atoms,
Z is BN(DO(C$_d$H$_{2d}$O)$_e$R)$_{2-z}$V$_z$,
each d is 2 to 4,
each e is 0 to 15,
z=0 to 2,
V is selected from the group consisting of alkyl of less than 8 carbon atoms which may be optionally substituted with hydroxyl and alkylamine, the nitrogen of which may be optionally alkoxylated or substituted with alkyl,
D is a divalent alkylene bridging group of 2 to 6 carbon atoms on which there may be hydroxyl substituents, and
B is a divalent alkylene group of 2 to 4 carbon atoms or D(O)$_j$(C$_d$H$_{2d}$O)$_j$D, wherein j is 0 to 8 and is 0 or 1.

2. The process of claim 1 wherein the composition additionally comprises an acid function pesticide.

3. The process of claim 2 where the amino siloxane alkoxylate is present in the composition at a concentration between 0.01% and 95.0% by weight.

4. The process according to claim 3 where the acid functional pesticide is selected from, growth regulators, photosynthesis inhibitors, pigment inhibitors, mitotic disrupters, lipid biosynthesis inhibitors, cell wall inhibitors, and cell membrane disrupters.

5. The process according to claim 3 wherein the acid functional pesticide is an herbicide selected from the group consisting of: phenoxy acetic acids, phenoxy propionic acids, phenoxy butyric acids, benzoic acids, triazines, and 5-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, glufosinate, sulfonylureas, imidazolinones, clethodim, diclofop-methyl, fenoxaprop ethyl, fluazifop-p-butyl, haloxyfop-methyl, quizalofop, sethoxydim, dichlobenil, isoxaben, and bipyridylium compounds.

6. The process according to claim 1 wherein the composition additionally comprises a nonionic siloxane of the formula

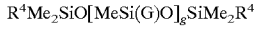

R$^4$Me$_2$SiO[MeSi(G)O]$_g$SiMe$_2$R$^4$ wherein
g=0 to 2,
G=C$_a$H$_{2a}$O(C$_2$H$_4$O)$_t$(C$_3$H$_6$O)$_w$R,
a and R are as defined in claim 1,
t=3 to 12,
w=0 to 8, and
R$^4$ is G, or an alkyl of one to four carbons.

7. The process according to claim 6 wherein the weight ration of the nonionic siloxane to the amino siloxane alkoxylate is between 5:95 and 95:5.

8. The process according to claim 6 wherein R$^4$ is methyl.

9. The process according to claim 6 wherein g=1.

10. The process according to claim 1 wherein Z is CH$_2$CH$_2$CH$_2$OCH$_2$CH(OH)CH$_2$N(C$_2$H$_4$OH)$_2$.

11. The process according to claim 1 wherein a=3, b=1 to 8, c=0 to 5 and b+c=4 to 8.

12. The process according to claim 11 wherein z=1 and V is an alkyl which may be substituted with a hydroxyl functionality.

13. The process according to claim 11 wherein z is 1 or 2.

14. The process according to claim 11 wherein B is $D(O)_y(C_dH_{2d}O)_jD$, wherein j=0 to 6 and y is 0 or 1.

15. The process according to claim 14 wherein j=0 to 2.

16. The process according to claim 14 wherein, in the group Z, R is hydrogen or methyl, D is a divalent organic group of 2 to 4 carbons, B is a divalent organic group of 2 to 4 carbons, in which at least one carbon radical contains a hydroxyl group, and V is 2-hydroxyethyl, 2-hydroxypropyl, 3-hydroxypropyl, propyl, ethyl or methyl.

17. The process as in claim 1 wherein the composition is an aqueous formulation further comprising a pesticide.

18. The process as in claim 17 wherein the composition is formulated by mixing water, a pesticide and an additive comprising said amino siloxane alkoxylate, the additive being added in an amount to provide the composition with from 0.01 to 5.0% by weight of said amino siloxane alkoxylate.

19. The process as in claim 18 wherein the additive is provided in an amount to provide from 0.025% to 0.5% of the amino siloxane alkoxylate in the composition.

20. The process as in claim 1 wherein the composition is applied by spraying.

21. The process as in claim 1 wherein the composition further comprises an oil diluent.

22. The process as in claim 1 wherein each e is 0 to 8.

* * * * *